United States Patent [19]

Mannino et al.

[11] Patent Number: 5,504,207
[45] Date of Patent: *Apr. 2, 1996

[54] PROCESS AND INTERMEDIATE FOR THE PREPARATION OF TERAZOSIN HYDROCHLORIDE DIHYDRATE

[75] Inventors: Anthony Mannino, Round Lake Beach; Rodger F. Henry, Waukegan; Wayne R. Heitmann, Lindenhurst; Bruce W. Horrom, Waukegan, all of Ill.

[73] Assignee: Abbott Laboratories, Abbott Park, Ill.

[ * ] Notice: The term of this patent shall not extend beyond the expiration date of Pat. No. 5,299,615.

[21] Appl. No.: 324,635

[22] Filed: Oct. 18, 1994

[51] Int. Cl.$^6$ .................. C07D 239/84; A61K 31/505
[52] U.S. Cl. ............................................. 544/291
[58] Field of Search ............................... 544/291

[56] References Cited

U.S. PATENT DOCUMENTS

| | | | |
|---|---|---|---|
| 4,026,894 | 5/1977 | Winn et al. | 260/256.4 |
| 4,112,097 | 9/1978 | Winn et al. | 424/251 |
| 4,251,532 | 2/1981 | Roteman | 424/251 |
| 4,816,455 | 3/1989 | Schikaneder et al. | 514/254 |
| 5,212,176 | 5/1993 | Kyncl et al. | 514/254 |
| 5,294,615 | 3/1994 | Meyer et al. | 514/254 |
| 5,362,730 | 11/1994 | Bauer et al. | 514/254 |

FOREIGN PATENT DOCUMENTS 5-078382  3/1993  Japan .

*Primary Examiner*—Cecilia Tsang
*Assistant Examiner*—King Lit Wong
*Attorney, Agent, or Firm*—Jerry F. Janssen

[57] ABSTRACT

A process for the preparation of 1-(4-amino-6,7-dimethoxy-2-quinazolinyl)-4-(2-tetrahydrofuroyl)piperazine hydrochloride (terazosin hydrochloride dihydrate comprises the steps of reacting 4-amino-2-chloro-6,7-dimethoxy-quinazoline with N-(2-tetrahydrofuroyl)piperazine in an anhydrous polar organic solvent in the absence of an added acid scavenger to produce anhydrous 1-(4-amino-6,7-dimethoxy-2-quinazolinyl)-4-(2-tetrahydrofuroyl)piperazine hydrochloride (Form IV) and thereafter converting the product of that step to 1-(4-amino-6,7-dimethoxy-2-quinazolinyl)-4-(2-tetrahydrofuroyl)-piperazine hydrochloride dihydrate.

4 Claims, 4 Drawing Sheets

PROCESS AND INTERMEDIATE FOR THE PREPARATION OF TERAZOSIN HYDROCHLORIDE DIHYDRATE

TECHNICAL FIELD

The present invention relates to a chemical process and to an intermediate chemical compound in that process. More particularly, the present invention concerns a process for preparing 1-(4-amino-6,7-dimethoxy-2-quinazolinyl)-4-(2-tetrahydrofuroylpiperazine ("terazosin") hydrochloride dihydrate and the intermediate compound of that process, designated the "Form IV" anhydrous crystalline modification of terazosin hydrochloride.

BACKGROUND OF THE INVENTION 1-(4-Amino-6,7-dimethoxy-2-quinazolinyl)-4-tetrahydrofuroylpiperazine hydrochloride is known by the common name "terazosin" and is the subject of U.S. Pat. No. 4,026,894.

Pharmaceutical compositions comprising terazosin or a pharmaceutically acceptable salt: and the use of such compositions for the treatment of hypertension are disclosed and claimed in U.S. Pat. No. 4,112,097.

The dihydrate of terazosin, its preparation, pharmaceutical compositions containing the dihydrate, and their use for the treatment of hypertension are disclosed and claimed in U.S. Pat. No. 4,251,532.

U.S. Pat. No. 5,212,176 discloses and claims the R(+)-enantiomer of terazosin hydrochloride dihydrate, pharmaceutical compositions containing the R(+)-enantiomer, and their use in the treatment of hypertension, benign prostatic hyperplasia, hyperinsulinemia, and congestive heart failure.

The Form II crystalline modification of anhydrous terazosin hydrochloride is the subject of U.S. Pat. No. 5,294,615 and processes for its preparation are disclosed in the continuation-in-part, U.S. Pat. No. 5,362,730.

The Form III crystalline modification of anhydrous terazosin hydrochloride and the crystalline methanolate of terazosin hydrochloride are the subjects of U.S. Pat. No. 5,412,095.

SUMMARY OF THE INVENTION

Figure 1:
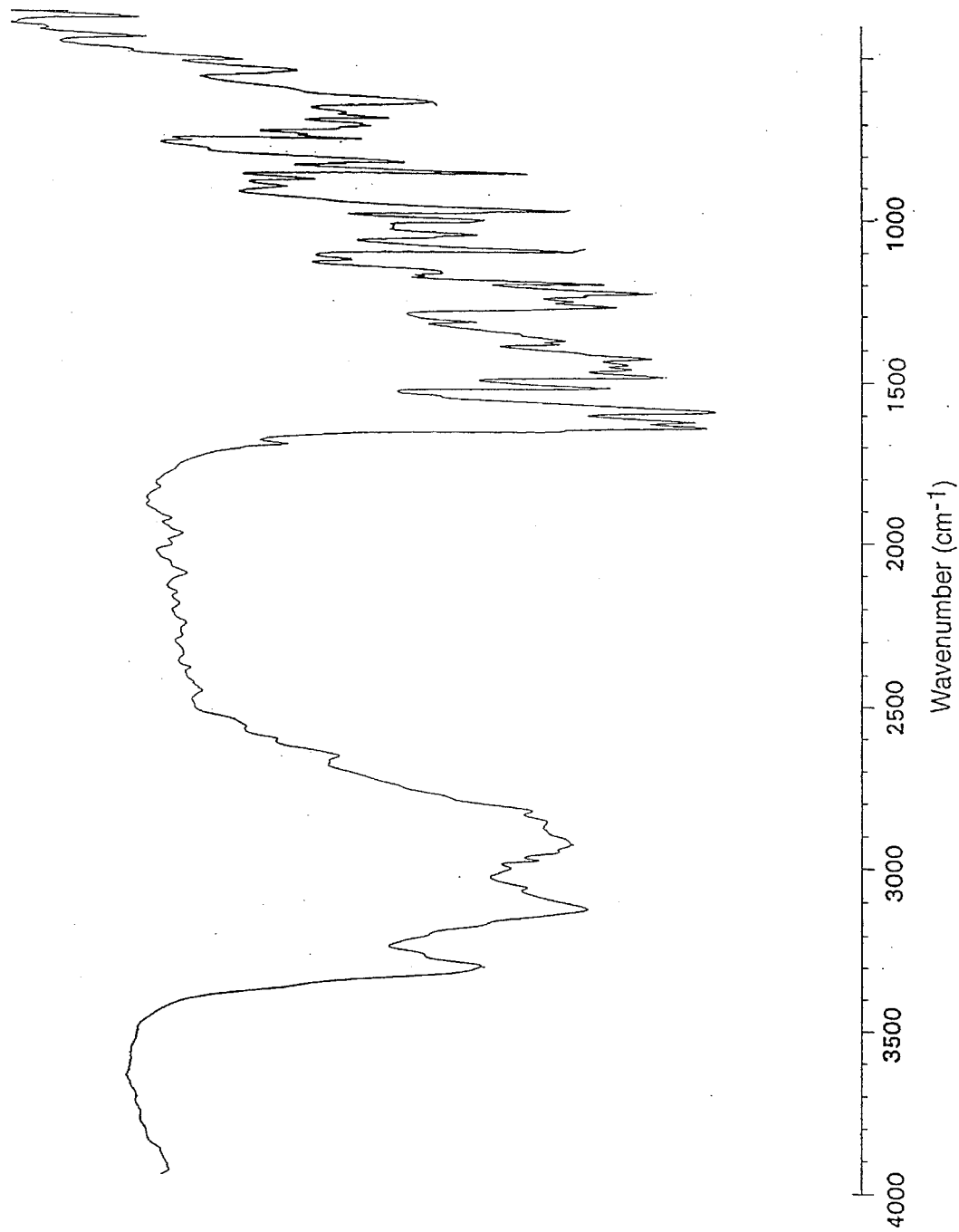
FIG. 1 is the infrared spectrum of the Form IV crystalline modification of anhydrous terazosin hydrochloride which is produced as an intermediate in the process of the present invention.

In its principal embodiment, the present invention comprises a process for the preparation of 1-(4-amino-6,7-dimethoxy-2-quinazolinyl)-4-(2-tetrahydrofuroyl)piperazine hydrochloride dihydrate comprising the steps of a) reacting 4-amino-2-chloro-6,7-dimethoxyquinazoline with N-(2-tetrahydrofuroyl)-piperazine in an anhydrous polar organic solvent in the absence of an added acid scavenger to produce the Form IV crystalline modification of anhydrous 1-( 4-amino-6,7-dimethoxy-2-quinazolinyl)-4-(2-tetrahydrofuroyl)piperazine hydrochloride; and b) thereafter converting the product of Step a) to 1-(4-amino- 6,7-dimethoxy-2-quinazolinyl)-4-(2-tetrahydrofuroyl)piperazine hydrochloride dihydrate.

In another embodiment, the present invention provides the novel anhydrous crystalline modification of 1-(4-amino-6,7-dimethoxy-2-quinazolinyl)-4-(2-tetrahydrofuroyl)piperazine hydrochloride characterized by principal peaks in the powder X-ray diffraction pattern at values of 7.15°±0.2°; 10.44±0.2°; 14.56±0.2; 20.48±0.2°; 21.23±0.2°; 22.47±0.2°; 23.70±0.2°; 24.43±0.2°; and 27.11±0.2°; of two theta (designated the "Form IV" crystalline modification of anhydrous terazosin hydrochloride).

DETAILED DESCRIPTION AND PREFERRED EMBODIMENTS

The process of the present invention provides an efficient, high-yield, environmentally-friendly process for preparing terazosin hydrochloride dihydrate by passing through the novel "Form IV" crystalline modification of anhydrous terazosin hydrochloride rather than the base form of terazosin as taught in U.S. Pat. No. 4,251,532. The process comprises coupling 4-amino-2-chloro- 6,7-dimethoxyquinazoline with 1-(2-tetrahydrofuroyl)piperazine in an anhydrous polar organic solvent in the absence of an added acid scavenger in the temperature range of between about 100°–150° C., preferably about 110°–1300° C. The reaction may be run effectively in solvents such as $C_1$–$C_4$ alcohols, $C_2$–$C_4$ ether-alcohols, $C_4$–$C_8$ diethers and $C_3$–$C_6$ ketones. Since the reaction is most conveniently carried out by heating the reaction mixture under reflux, dry polar organic solvents having a boiling point in the temperature range of between 100°–150° C. are preferred. A particularly preferred solvent is the monomethyl ether of ethylene glycol (i.e. methoxyethanol) having a boiling point of about 125° C.

By the term "ether-alcohol" is meant a monoether of a diol and includes such compounds as methoxyethanol, methoxypropanol, ethoxyethanol and the like.

The term "diether" is meant the diether derivative of a diol and includes such compounds as dimethoxymethane, dimethoxyethane, dimethoxypropane, diethoxymethane, diethoxyethane, and the like.

The initial coupling reaction step of the process of the present invention is carried out for a period of time sufficient to effect essentially complete reaction of the starting materials, generally for a period of time ranging between about six to twelve hours, most preferably for a period of about eight hours.

The process of the present reaction is characterized by carrying out the coupling reaction between the chloroquinazoline and the substituted piperazine compound in the absence of an added acid scavenger. The prior art process employs triethylamine to scavenge the hydrogen chloride which is the by-product of the coupling reaction. Because of its use of triethylamine, the prior art process results in the production, from this first coupling step, of the base form of terazosin which is contaminated with triethylammonium chloride. As a consequence, this process, which is illustrated in Example 1 below, includes a number of subsequent processing steps which involve pH adjustment and filtration to separate the terazosin base from the triethylammonium chloride reaction by-product. These steps add to the complexity of the prior art process with attendant decrease in yield and through-put and increase in the volumes of waste materials. Moreover, since the product of the initial coupling reaction in the prior art process is the base form of terazosin, subsequent process steps are required to convert the base to the desired hydrochloride and convert it to the dihydrate crystalline form.

Second, the elimination of a number of process steps compared with the prior art process greatly reduces the volume of the waste stream, minimizing the volumes of acid and organic solvents required per mol of product and completely eliminating the need for caustic reagents. Indeed, the process of the present invention eliminates the use of triethylamine, a potentially hazardous air pollutant.

Third, the process of the present invention provides greater throughput. Using batch processing, the present process requires about four days for the preparation of a batch of terazosin hydrochloride dihydrate, compared with about seven days for preparation of a batch using the prior art process. The effect is to greatly diminish the length of time commercial processing equipment is "tied up" to prepare batches of terazosin hydrochloride dihydrate.

TABLE 1

Comparison of the Present and Prior Art Processes for the Preparation of Terazosin Hydrochloride

| | Percent Yield | Triethylamine (Grams per mol of Starting Material) | 2-Methoxyethanol (Kg. per mol of Starting Material) | Ethanol (Liters per mol of Starting Material) | Acidic Waste (Liters per mol of Starting Material) | Basic Waste (Liters per mol of Starting Material) |
|---|---|---|---|---|---|---|
| Prior Art Process | ~73% | 152 | 2 | 5.8 | 5.8 | 7.7 |
| Present Process | ~92% | 0 | 0.7 | 1.1 | 2.5 | 0 |

As one example of its greater complexity, the prior art process includes the s step of completely removing the solvent at the end of the first coupling step. While not holding to one theory to the exclusion of others, it is believed that the removal of the solvent from the first coupling step in the prior art process is required to minimize loss of a portion of the intermediate base coupling product which would otherwise occur if the product were simply filtered from the solution. That is to say, if the terazosin base were simply filtered from the initial reaction mixture, or filtered from a concentrated reaction mixture, the solubility of the base in the reaction solvent is sufficiently great to cause the loss of an appreciable portion in the filtrate.

By eliminating the addition of an acid scavenger to the initial coupling reaction mixture, the first step of the process of the present invention proceeds smoothly and results directly in the production of a high yield of anhydrous terazosin hydrochlofide. Because this intermediate is an ionic salt and has considerably lower solubility in the reaction solvent than the corresponding base, it can be easily and almost completely separated from the reaction mixture by filtration without the need to remove the reaction solvent. All that remains to produce the desired end-product is the subsequent conversion, in the second step of the process of the present invention, of the anhydrous terazosin hydrochloride to its dihydrate form. This is effected conveniently and in high yield by recrystallization of the anhydrous Form IV of terazosin hydrochloride from the first step from aqueous ethanol.

As can be seen by the data presented in Table 1, the process of the present invention presents a number of advantages over the prior art process for preparing terazosin hydrochloride dihydrate. First, the yield is considerably increased. The prior art process results in about 73% overall yield from the starting 4-amino- 2-chloro-6,7-dimethoxyquinazoline, while the process of the present invention results in an overall yield of about 92%.

Surprisingly, it has been found that the intermediate anhydrous terazosin hydrochloride which results from the first coupling step of the process of this invention is a heretofore unkown crystalline modification. To distinguish this is material from the anhydrous forms of terazosin hydrochloride previously known (i.e. Form I, U.S. Pat. No. 4,026,894; Form II, U.S. Pat. No. 5,294,615; and Form III, U.S. Pat. No. 5,412,095.) the intermediate produced in the first coupling step of the process of this invention is designated "Form IV" of anhydrous terazosin hydrochloride.

Figure 2:
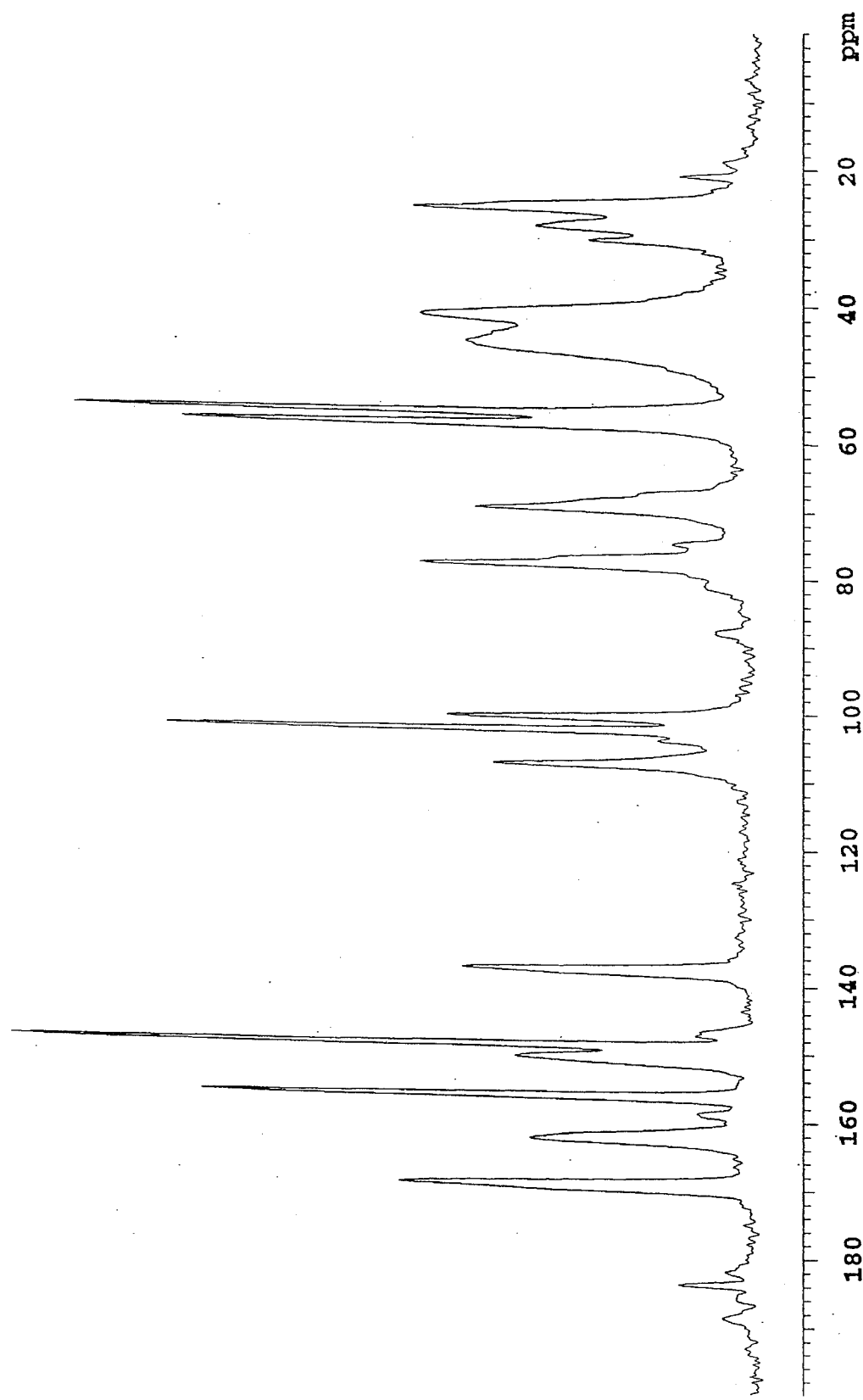
FIG. 2 is the 75.431 MHz nuclear magnetic resonance spectrum of the Form IV crystalline modification of anhydrous terazosin hydrochloride which is produced as an intermediate in the process of the present invention.
Figure 3:
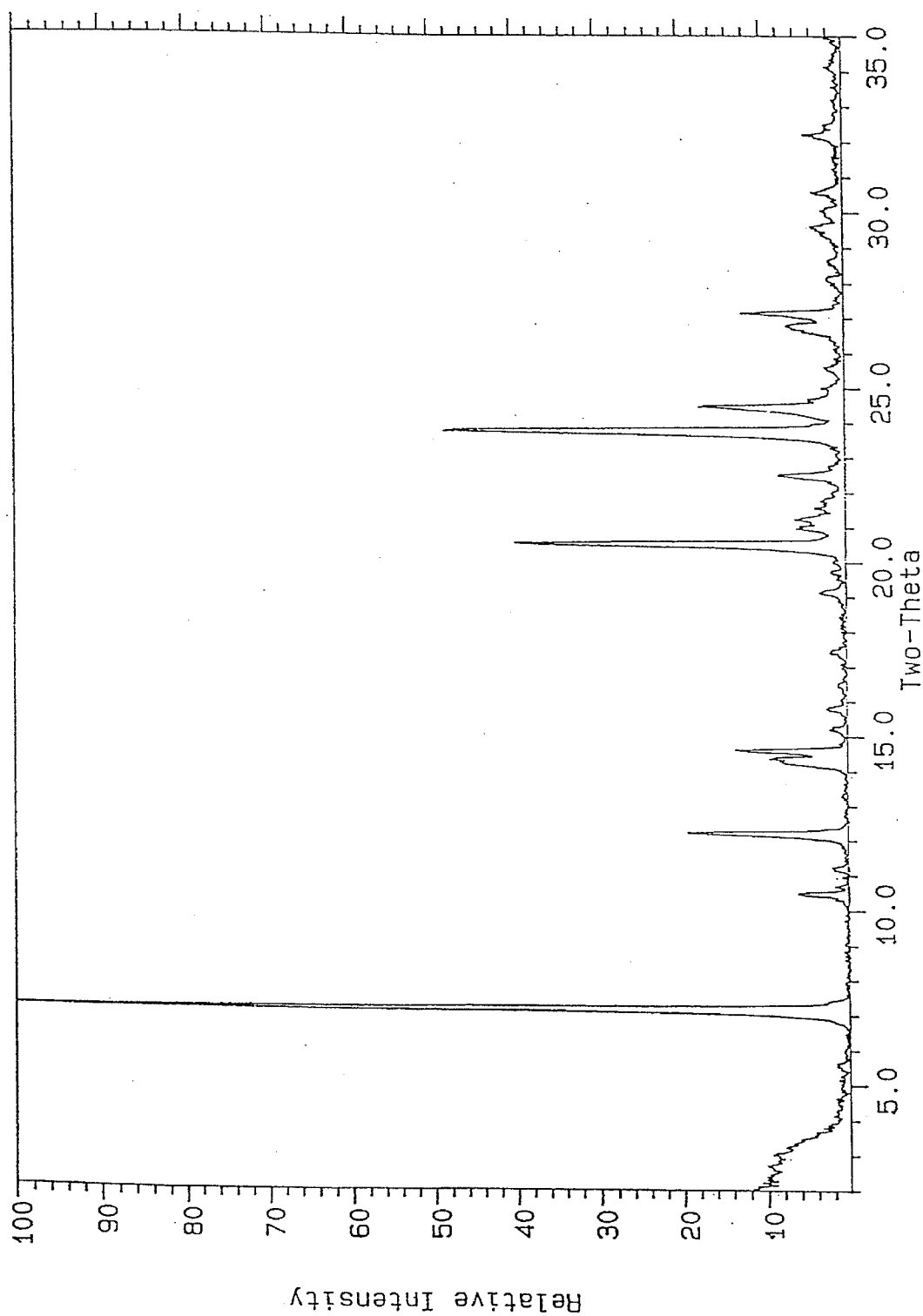
FIG. 3 is the powder X-ray diffraction pattern (trace) of the Form IV crystalline modification of anhydrous terazosin hydrochloride which is produced as an intermediate in the process of the present invention.
Figure 4:
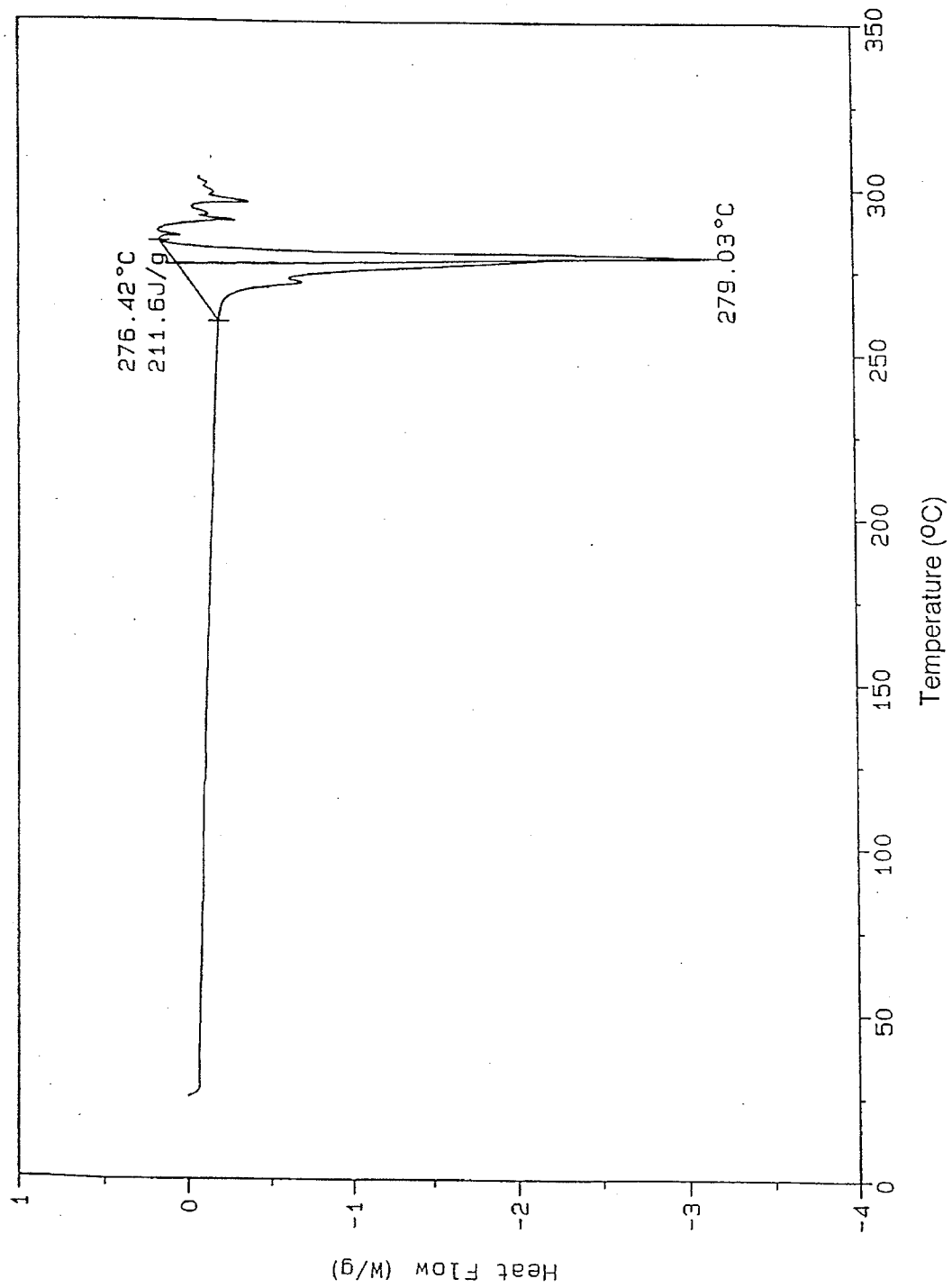
FIG. 4 is the differential scanning thermogram trace of the Form IV crystalline modification of anhydrous terazosin hydrochloride which is produced as an intermediate in the process of the present invention.

This intermediate is characterized by its infrared and nuclear magnetic resonance spectra and the powder X-ray and differential scanning thermogram traces appear in FIGS. 1–4, respectively.

In Examples 1–3 below, a comparison is made between the process of the prior art and that of the present invention. In Example 1, the prior art process for preparing terazosin hydrochloride dihydrate which appears in U.S. Pat. No. 4,251,532 is presented. Example 3 illustrates the process of the present invention. In Example 2, the process of U.S. Pat. No. 4,251,532 is repeated with the sole change of eliminating the triethylamine acid scavenger.

As can be seen by examining Example 2, the simple elimination of the acid scavenger from the prior art process without the other changes which comprise the process of the present invention results in an overall yield of terazosin hydrochloride dihydrate of about 65% which compares roughly with the 73% overall yield disclosed in the prior art. When the process of the present invention is employed for the preparation of terazosin hydrochloride, as illustrated by Example 3, the overall yield of terazosin hydrochloride dihydrate is increased to about 92%.

EXAMPLE 1

Prior Art Process (U.S. Pat. No. 4,251,532)

Step 1-Preparation of 1-(4-Amino-6,7-dimethoxy-2-quinazolinyl)-4-(2-tetrahydrofuroyl)piperazine Sixty grams (0.25 tool) of 4-amino-2-chloro-6,7-dimethoxyquinazoline and 56.8 grams (0.308 tool) of N-(2-tetrahydrofuroyl)piperazine were added to a stirred solution of 500 grams of Methyl Cellosolve® (ethylene glycol monomethyl ether) and 37.9 grams of triethylamine. The reaction mixture was heated to and maintained at a temperature of between 115° C. to 120° C. for 8 hours, and then allowed to cool to room temperature overnight. The Methyl Cellosolve® was removed by vacuum distillation, the residue was taken up in 1920 ml of 45° C. distilled water, and the temperature of the solution was readjusted to 45° C. The pH was then adjusted to pH 2.5 with concentrated hydrochloric acid and the solution mixed for 1 hour. The solution was then filtered and the pH adjusted to pH 8.3 with filtered ammonia water (28%). After heating for one hour at 65° C., the solution was cooled to 15° C. and held at a temperature of between 15°C. –20° C. for 16 hours. The resulting crystalline product was filtered, washed with cold water (15° C.) and dried in vacuo at 65° C. to yield 84 grams (87%) of anhydrous base.

Step 2-Preparation of 1-(4-Amino-6,7-dimethoxy-2-quinazolinyl)4-(2-tetrahydrofuroyl)piperazine hydrochloride dihydrate The hydrochloride salt of the dihydrate of the compound prepared as described above in Step 1 was prepared by slurrying 10 grams (0.026 tool) of the above-prepared 1-(4-amino-6,7-dimethoxy-2-quinazolinyl)-4-(2-tetrahydrofuroyl)piperazine in 150 ml of 190 proof Formula 3A alcohol, heating the slurry to about as 35° C., adding 2.5 ml of concentrated aqueous hydrochloric acid, and heating the mixture to about 70° C. The reaction mixture was carbon treated, the carbon was filtered off and the filtrate was cooled overnight in an icebox. The product was then filtered off and dried at 60° C. to obtain 10 grams (0.022 mol, 84%) of the desired product, m.p. 271°–274° C.

The overall yield from the starting 4-amino-2-chloro-6,7-dimethoxy-quinazoline was 73%.

EXAMPLE 2

Modified Prior Art Process

Preparation of 1-(4-Amino,6,7-dimethoxy-2-quinazolinyl)-4-(2-tetrahydrofuroyl)-piperazine hydrochloride dihydrate The process of U.S. Pat. No. 4,251,532 was repeated with the sole exception that in Step 1 leading to the formation of the 1-(4-amino-6,7-dimethoxy-2-quinazolinyl)-4-(2-tetrahydrofuroyl)piperazine fee base, the triethylamine acid scavenger was excluded.

Step 1-Preparation of 1-(4-Amino-6,7-dimethoxy-2-quinazolinyl)-4-(2-tetrahydrofuroyl)piperazine Sixty grams (0.25 tool) of 4-amino-2-chloro-6,7-dimethoxyquinazoline and 56.8 grams (0.308 mol) of N-(2-tetrahydrofuroyl)piperazine were added to a stirred solution of 500 grams of Methyl Cellosolve® (ethylene glycol monomethyl ether). The reaction mixture was heated to and maintained at a temperature of between 115° C. to 120° C. for 8 hours, and then cooled to 60° C. The Methyl Cellosolve® was removed by vacuum distillation, the residue was taken up in 1920 ml of 45° C. distilled water, and the temperature of the solution was readjusted to 45° C. The pH was then adjusted to pH 2.5 with concentrated hydrochloric acid and the solution mixed for 1 hour. The solution was then filtered and the pH adjusted to pH 8.3 with filtered ammonia water (28%). After heating for one hour at 65° C., the solution was cooled to 15° C. and held at a temperature of between 15°–20° C. for 16 hours. The resulting crystalline product was filtered, washed with cold water (15° C.) and dried in vacuo at 65° C. to yield 90.8 grams (94%) of anhydrous base.

Step 2- Preparation of 1-(4-Amino-6,7-dimethoxy-2-quinazolinyl)-4-(2-tetrahydrofuroyl)piperazine hydrochloride dihydrate The hydrochloride salt of the dihydrate of the compound prepared as described above in Step 1 was prepared by slurrying 10 grams (0.026 mol) of the above-prepared 1-(4-amino-6,7-dimethoxy-2-quinazolinyl)-4-( 2-tetrahydrofuroyl)-piperazine in 150 ml of 190 proof Formula 3A alcohol, heating the slurry to about 35° C., adding 2.5 ml of concentrated aqueous hydrochloric acid, and heating the mixture to about 70° C. The reaction mixture was carbon treated, the carbon was filtered off and the filtrate was cooled overnight in an icebox. The product was then filtered off and dried at 60° C. to obtain 8.3 grams (0.018 tool, 69%) of the desired product.

The overall yield from the starting 4-amino-2-chloro-6,7-dimethoxy-quinazoline was 65%.

EXAMPLE 3

Method of this Invention

Preparation of 1-(4-Amino-6,7-dimethoxy-2-quinazolinyl)-4-(2-tetrahydrofuroyl)-piperazine hydrochloride dihydrate

Step 1- Preparation of Anhydrous 1-(4-amino-6,7-dimethoxy-2-quinaolinyl)-4-(2-tetrahydrofuroyl)piperazine hydrochloride A slurry of 60 grams (0.25 mol) of 4-amino-2-chloro-6,7-dimethoxy-quinazoline, 55.3 g (0.3 tool) of 1-(2-tetrahydrofuroyl)piperazine and 175 grams of 2-methoxyethanol was heated, under a nitrogen atmosphere with mechanical stirring, to 120°–123° C. for eight hours. The slurry was then cooled to 70° C. and 140 ml of 3A 200 proof ethanol was added. The resulting mixture was heated to 60°–70° C. for one hour and then cooled to 0°–5° C. To the cooled solution was added 2.5 g of concentrated aqueous hydrochloric acid in 12 ml of 3A 200 proof ethanol. This mixture was kept at –5°–5° C. for one and one-half hours after which the precipitated solid was collected by filtration and washed with 50 ml of cold 3A 200 proof ethanol to yield 98.7 g (0.233 tool, 93%) of anhydrous 1-(4-amino- 6,7-dimethoxy-2-quinazolinyl)-4-(2-tetrahydrofuroyl)piperazine hydrochloride of a previously unknown crystalline modification.

The infrared and nuclear magnetic resonance spectra and the powder X-ray and differential scanning thermogram traces appear in FIGS. 1–4, respectively.

Step 2-1-(4-Amino-6,7-dimethoxy-2-quinazolinyl)-4-(2-tetrahydrofuroyl)-piperazine hydrochloride dihydrate To a mixture of 296 ml of distilled water and 166 ml of 3A 200 proof ethanol at 55° C. were added 97.6 grams (0.23 1 tool) of 1-(4-amino- 6,7-dimethoxy-2-quinazolinyl)-4-(2-tetrahydrofuroyl)piperazine hydrochloride, prepared as as described above in Step 1.

The mixture was warmed to 78° C. and then treated with 3 grams of diatomaceous earth. After stirring for five minutes, the mixture was filtered and the filter cake was washed with 25 ml of hot distilled water. The filtrate was cooled and held at 30° C. for one hour. To the resulting slurry was added over a period of 32 minutes 148 ml of 3A 200 proof ethanol. The resulting mixture was cooled to 10° C. and the pH was adjusted to 2.0 by the addition of 3.8 grams of concentrated aqueous hydrochloric acid. The acidic solution was cooled to 0°–5° C. and held in that temperature range for sixteen hours.

The precipitated solid was collected by filtration and dried in a vacuum oven at 50°–55° C. at 127 mm Hg for twenty hours to yield 105 g (0.229 tool, 99%) of 1-(4-amino-6,7-dimethoxy-2-quinazolinyl)-4-( 2-tetrahydrofuroyl)piperazine hydrochloride dihydrate.

The overall yield from the starting 4-amino-2-chloro6,7-dimethoxy-quinazoline was 92%.

We claim:

1. A process for the preparation of 1-(4-amino-6,7-dimethoxy- 2-quinazolinyl)-4-(2-tetrahydrofuroyl)piperazine hydrochloride dihydrate comprising the steps of a) reacting 4-amino-2-chloro-6,7-dimethoxyquinazoline with N-(2-tetrahydrofuroyl)piperzine in a ratio of 1 to n where n is up to 1.2 in an anhydrous polar organic solvent in the absence of an added acid scavenger to produce the Form IV crystalline modification of anhydrous 1-(4-amino-6,7-dimethoxy-2-quinazolinyl)-4-(2-tetrahydrofuroyl)-piperazine hydrochloride; and b) thereafter converting the product of Step a) to 1-(4-amino- 6,7-dimethoxy-2-quinazolinyl)-4-(2-tetrahydrofuroyl)piperazine hydrochloride dihydrate.

2. The process of claim 1 wherein said anhydrous polar organic solvent is selected from $C_1$–$C_4$ alcohols, $C_1$–$C_4$ ether-alcohols, $C_4$–$C_8$ diethers and $C_3$–$C_6$ ketones.

3. The process of claim 3 wherein said anhydrous polar organic solvent is methoxyethanol.

4. The anhydrous Form IV crystalline modification of 1-(4-amino- 6,7-dimethoxy-2-quinazolinyl)-4-(2-tetrahydrofuroyl)piperazine hydrochloride characterized by principal peaks in the powder X-ray diffraction pattern at values of 7.15°±0.2°; 10.44±0.2°; 14.56±0.2°; 20.48±0.2°; 21.23±0.2°; 22.47±0.2°; 23.70±0.2°; 24.43±0.2°; and 27.11±0.2°; of two theta.

\* \* \* \* \*

UNITED STATES PATENT AND TRADEMARK OFFICE
CERTIFICATE OF CORRECTION

PATENT NO. : 5,504,207
DATED : April 2, 1996
INVENTOR(S) : A. Mannino, et

It is certified that error appears in the above-indentified patent and that said Letters Patent is hereby corrected as shown below:

Column 1, line 25, change "salt:" to --salt--.

Column 2, line 21, change "14.56 ± 0.2;" to --14.56 ± 0.2°;--.

Column 2, line 39, change "110°-1300°'" to --110°-130°--.

Column 3, line 31, please delete "s".

Column 4, line 35, please delete "is".

Column 5, line 66, change "fee base" to --free base--.

Column 5, line 12, change "tool" to --mol--.

Column 5, line 13, change "tool" to --mol--.

Column 5, line 16, change "tricthylaminc" to --triethylamine--.

Column 5, line 40, change "tool" to --mol--.

Column 5, line 43, please delete "as".

UNITED STATES PATENT AND TRADEMARK OFFICE
CERTIFICATE OF CORRECTION

PATENT NO. : 5,504,207
DATED : April 2, 1996
INVENTOR(S) : A. Mannino, et al.

Page 2 of 3

It is certified that error appears in the above-indentified patent and that said Letters Patent is hereby corrected as shown below:

Column 5, line 59, change "1-(4-Amino,6" to --1-(4-Amino-6--.

Column 6, line 5, change "tool" to --mol--.

Column 6, line 55, change "quinaolinyl" to --quinazolinyl--.

Column 6, line 58, change "tool" to --mol--.

Column 7, line 3, change "tool" to --mol--.

Column 7, lines 10-11, change
"Step
2-1-(4-Amino-6,7-dimethoxy-2-quinazolinyl)-4-" to
--Step 2
1-(4-Amino-6,7-dimethoxy-2-quinazolinyl)-4- --.

Column 7, line 17, change "tool" to --mol--.

Column 7, line 18, please delete the first "as".

Column 7, line 33, change "tool" to --mol--.

UNITED STATES PATENT AND TRADEMARK OFFICE
CERTIFICATE OF CORRECTION

PATENT NO. : 5,504,207
DATED : April 2, 1996
INVENTOR(S) : A. Mannino, et al.

It is certified that error appears in the above-indentified patent and that said Letters Patent is hereby corrected as shown below:

Column 8, line 21, change (second occur.) "$C_1 - C_4$" to --$C_2 - C_4$--.

Column 8, line 23, change "claim 3" to --claim 2--.

Signed and Sealed this

Third Day of December, 1996

Attest:

BRUCE LEHMAN

Attesting Officer   Commissioner of Patents and Trademarks

UNITED STATES PATENT AND TRADEMARK OFFICE
CERTIFICATE OF CORRECTION

PATENT NO. : 5,504,207
DATED : April 2, 1996
INVENTOR(S) : A. Mannino, *et al.*

It is certified that error appears in the above-indentified patent and that said Letters Patent is hereby corrected as shown below:

Title page, replace:

"Notice: The term of this patent shall not extend beyond the expiration date of Pat. No. 5,299,615."

with:

--Notice: The term of this patent shall not extend beyond the expiration date of Pat. No. 5,294,615.--

Signed and Sealed this

Thirteenth Day of May, 1997

*Attest:*

BRUCE LEHMAN

*Attesting Officer*  Commissioner of Patents and Trademarks